(12) United States Patent
Kim et al.

(10) Patent No.: US 12,014,735 B2
(45) Date of Patent: Jun. 18, 2024

(54) EMOTION ADJUSTMENT SYSTEM AND EMOTION ADJUSTMENT METHOD

(71) Applicants: Hyundai Motor Company, Seoul (KR); Kia Corporation, Seoul (KR)

(72) Inventors: Ki Chang Kim, Gyeonggi-do (KR); Dong Chul Park, Gyeonggi-Do (KR); Tae Kun Yun, Gyeonggi-Do (KR); Jin Sung Lee, Gyeonggi-do (KR)

(73) Assignees: Hyundai Motor Company, Seoul (KR); Kia Corporation, Seoul (KR)

( * ) Notice: Subject to any disclaimer, the term of this patent is extended or adjusted under 35 U.S.C. 154(b) by 362 days.

(21) Appl. No.: 17/390,119

(22) Filed: Jul. 30, 2021

(65) Prior Publication Data
US 2022/0148589 A1 May 12, 2022

(30) Foreign Application Priority Data

Nov. 6, 2020 (KR) .......................... 10-2020-0147570

(51) Int. Cl.
*G10L 25/63* (2013.01)
*G10L 15/22* (2006.01)

(52) U.S. Cl.
CPC .............. *G10L 15/22* (2013.01); *G10L 25/63* (2013.01); *G10L 2015/223* (2013.01)

(58) Field of Classification Search
None
See application file for complete search history.

(56) References Cited

U.S. PATENT DOCUMENTS

| 8,086,449 | B2 * | 12/2011 | Ishii | ......................... G10L 25/90 704/207 |
| 2010/0070283 | A1 * | 3/2010 | Kato | ........................ G10L 21/02 704/E21.001 |
| 2011/0282666 | A1 * | 11/2011 | Washio | .................... G10L 25/48 704/246 |
| 2012/0166195 | A1 * | 6/2012 | Hayakawa | ............... G10L 17/26 704/240 |

(Continued)

FOREIGN PATENT DOCUMENTS

| JP | H 09-206291 A | 8/1997 |
| KR | 10-2017-0014050 A | 2/2017 |

(Continued)

*Primary Examiner* — Seong-Ah A Shin
(74) *Attorney, Agent, or Firm* — Fox Rothschild LLP

(57) ABSTRACT

An emotion adjustment system for determining a user's emotions based on a user's voice includes: a microphone configured to receive the user's voice; a controller configured to extract a plurality of sound quality factors in response to processing the user's voice, calculate a depression index of the user based on at least one sound quality factor among the plurality of sound quality factors, identify an emotional state of the user as a depressive state when the depression index is a preset value or more, determine the depressive state as a first state or a second state based on a correlation between at least two sound quality factors among the plurality of sound quality factors, and transmit a control command corresponding to the emotional state of the user identified as the first state or the second state; and a feedback device configured to perform an operation corresponding to the control command.

16 Claims, 6 Drawing Sheets

(56) References Cited

U.S. PATENT DOCUMENTS

| | | | |
|---|---|---|---|
| 2016/0019915 A1* | 1/2016 | Khan | G10L 19/018 |
| | | | 704/239 |
| 2017/0084295 A1* | 3/2017 | Tsiartas | G10L 17/08 |
| 2017/0206913 A1* | 7/2017 | Nahman | G10L 25/63 |
| 2017/0249438 A1* | 8/2017 | Jain | G16H 20/30 |
| 2018/0196432 A1* | 7/2018 | Krupat | A61B 5/6893 |
| 2018/0317876 A1* | 11/2018 | Emmanouilidou | G16H 40/63 |
| 2018/0366144 A1* | 12/2018 | Ashoori | G16H 40/63 |
| 2019/0142323 A1* | 5/2019 | Mitsuyoshi | G10L 25/03 |
| | | | 600/300 |
| 2019/0172458 A1* | 6/2019 | Mishra | G06V 10/82 |
| 2019/0253558 A1* | 8/2019 | Haukioja | G10L 15/22 |
| 2019/0325866 A1* | 10/2019 | Bromand | G06F 3/167 |
| 2020/0342057 A1* | 10/2020 | Boekweg | G10L 15/1815 |
| 2021/0315517 A1* | 10/2021 | Quatieri | A61B 7/008 |

FOREIGN PATENT DOCUMENTS

| | | |
|---|---|---|
| KR | 10-2020598 B1 | 9/2019 |
| KR | 10-2019-0131476 A | 11/2019 |
| KR | 10-2131391 B1 | 7/2020 |

* cited by examiner

EMOTION ADJUSTMENT SYSTEM AND EMOTION ADJUSTMENT METHOD

CROSS-REFERENCE TO RELATED APPLICATION

This application claims under 35 U.S.C. § 119 the benefit of Korean Patent Application No 10-2020-0147570, filed on Nov. 6, 2020 in the Korean Intellectual Property Office, the entire contents of which are incorporated herein by reference.

BACKGROUND

1. Technical Field

The present disclosure relates to an emotion adjustment system and an emotion adjustment method, more particularly, to the emotion adjustment system and the emotion adjustment method that can more precisely determine a user's emotions based on a user's voice.

2. Description of the Related Art

Recently, a technique for judging a user's emotion using various sensors has been actively studied. In addition, research on a technology that can induce a user's positive emotions by using it is also being actively conducted.

For example, an emotion adjustment system may provide a useful service to the user by determining a user's emotional state and providing several types of feedback devices that can perform actions reflecting the emotional state.

An example of the emotion adjustment system includes an artificial intelligence speaker or various devices and vehicles equipped with the same.

In particular, a vehicle may determine the emotional state of the user using various sensors such as a biosignal sensor, a microphone, and a camera, and provide feedback capable of alleviating or amplifying the user's emotions by using various feedback devices such as a vibrating element provided on a seat, a speaker, or an air conditioner.

However, according to recent technologies, additional components such as a biosignal sensor and a camera are required to determine the user's emotions, thereby increasing the cost. Further, such technologies merely determine whether the current emotional state of the user in the vehicle is positive or negative. In addition, based on whether the determined current emotional state is positive or negative, these technologies only provide feedback that adjusts an output of a component in a vehicle.

SUMMARY

Therefore, it is an aspect of the present disclosure to provide an emotion adjustment system and an emotion adjustment method that can specifically identify a user's emotion based on a user's voice and provide feedback corresponding to the user's emotion.

In accordance with one aspect of the disclosure, an emotion adjustment system includes: a microphone configured to receive a user's voice; a controller configured to extract a plurality of sound quality factors in response to processing the user's voice, calculate a depression index of the user based on at least one sound quality factor among the plurality of sound quality factors, identify an emotional state of the user as a depressive state when the depression index is a preset value or more, determine the depressive state as a first state or a second state based on a correlation between at least two sound quality factors among the plurality of sound quality factors, and transmit a control command corresponding to the emotional state of the user identified as the first state or the second state; and a feedback device configured to perform an operation corresponding to the control command.

The plurality of sound quality factors may include at least one of a sound pressure level, a loudness, a sharpness, a roughness, or a fluctuation strength.

The controller may be configured to calculate the depression index of the user based on at least one of the sound pressure level or the loudness.

The controller may be configured to calculate the depression index of the user based on a change pattern of the sound pressure level or the loudness.

The controller may be configured to calculate a noise index of the user's voice based on a correlation between the sharpness, the roughness, and the fluctuation strength, and determine the depressive state as the first state or the second state based on the noise index.

The noise index may include a rattle index and a squeak index, and the controller may be configured to determine the depressive state as the first state or the second state based on a ratio between the rattle index and the squeak index.

The controller may be configured to determine the depressive state as the first state when the rattle index is greater than the squeak index, and determine the depressive state as the second state when the squeak index is greater than the rattle index.

The feedback device may include a vibrating element, and the controller may be configured to transmit a first control command to cause the vibrating element to vibrate at a first frequency and a first intensity when the emotional state of the user is identified as the first state and transmit a second control command to cause the vibrating element to vibrate at a second frequency and a second intensity when the emotional state of the user is identified as the second state, and the first frequency may be less than the second frequency and the first intensity may be less than the second intensity.

The feedback device may include a speaker, and the controller may be configured to transmit a first control command to cause the speaker to play a first sound source when the emotional state of the user is identified as the first state and transmit a second control command to cause the speaker to play a second sound source when the emotional state of the user is identified as the second state, and a frequency band of the first sound source may be narrower than a frequency band of the second sound source.

The controller may be configured to identify the emotional state of the user as an instable state or a pleasant state when the depression index is less than the preset value, and transmit a control command corresponding to the emotional state of the user identified as the instable state or the pleasant state.

In accordance with one aspect of the disclosure, an emotion adjustment method includes: receiving, by a microphone, a user's voice; extracting, by a controller, a plurality of sound quality factors in response to processing the user's voice; calculating, by the controller, a depression index of the user based on at least one sound quality factor among the plurality of sound quality factors; identifying, by the controller, an emotional state of the user as a depressive state when the depression index is a preset value or more; determining, by the controller, the depressive state as a first state or a second state based on a correlation between at least two sound quality factors among the plurality of sound quality factors; transmitting, by the controller, a control command corresponding to the emotional state of the user identified as the first state or the second state; and performing, by a feedback device, an operation corresponding to the control command.

The plurality of sound quality factors may include at least one of a sound pressure level, a loudness, a sharpness, a roughness, or a fluctuation strength.

The calculating the depression index of the user may include: calculating the depression index of the user based on at least one of the sound pressure level or the loudness.

The calculating the depression index of the user may include: calculating the depression index of the user based on a change pattern of the sound pressure level or the loudness.

The determining the depressive state as a first state or a second state may include: calculating a noise index of the user's voice based on a correlation between the sharpness, the roughness, and the fluctuation strength; and determining the depressive state as the first state or the second state based on the noise index.

The noise index may include a rattle index and a squeak index, and the determining the depressive state as the first state or the second state based on the noise index may include: determining the depressive state as the first state or the second state based on a ratio between the rattle index and the squeak index.

The determining the depressive state as the first state or the second state based on the ratio between the rattle index and the squeak index may include: determining the depressive state as the first state when the rattle index is greater than the squeak index, and determining the depressive state as the second state when the squeak index is greater than the rattle index.

The feedback device may include a vibrating element, and the transmitting the control command corresponding to the emotional state of the user identified as the first state or the second state may include: transmitting a first control command to cause the vibrating element to vibrate at a first frequency and a first intensity when the emotional state of the user is identified as the first state; and transmitting a second control command to cause the vibrating element to vibrate at a second frequency and a second intensity when the emotional state of the user is identified as the second state, and the first frequency may be less than the second frequency and the first intensity may be less than the second intensity.

The feedback device may include a speaker, and the transmitting the control command corresponding to the emotional state of the user identified as the first state or the second state may include: transmitting a first control command to cause the speaker to play a first sound source when the emotional state of the user is identified as the first state; and transmitting a second control command to cause the speaker to play a second sound source when the emotional state of the user is identified as the second state, and a frequency band of the first sound source may be narrower than a frequency band of the second sound source.

The emotion adjustment method may further include: identifying the emotional state of the user as an instable state or a pleasant state when the depression index is less than the preset value; and transmitting a control command corresponding to the emotional state of the user identified as the instable state or the pleasant state.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
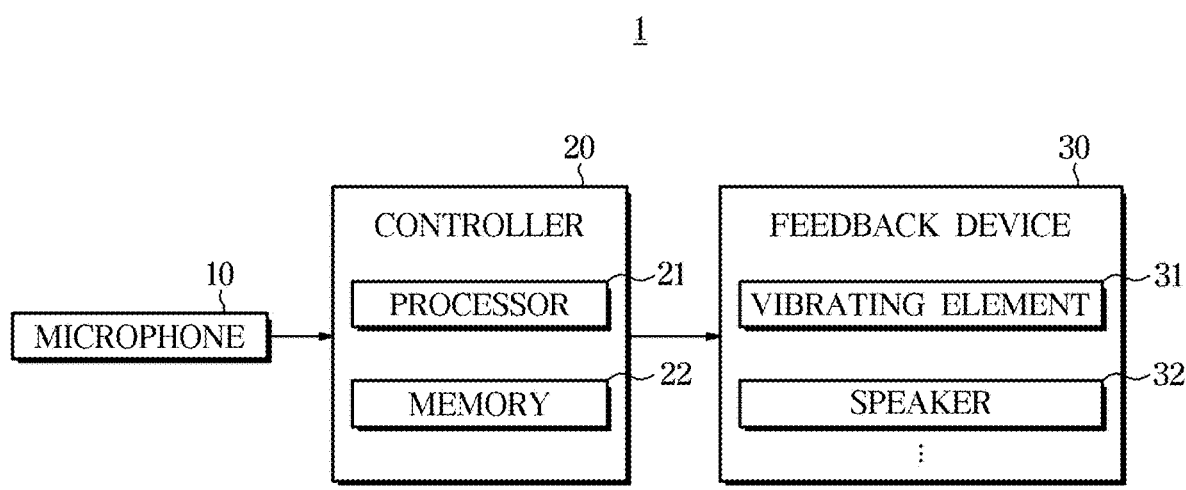
FIG. 1 is a control block diagram of an emotion adjustment system according to an embodiment.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unit", "-er", "-or", and "module" described in the specification mean units for processing at least one function and operation, and can be implemented by hardware components or software components and combinations thereof.

Further, the control logic of the present disclosure may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy disks, flash drives, smart cards and optical data storage devices. The computer readable medium can also be distributed in network coupled computer systems so that the computer readable media is stored and executed in a distributed fashion, e.g., by a telematics server or a Controller Area Network (CAN).

It will be understood that when an element is referred to as being "connected" another element, it may be directly or indirectly connected to the other element, wherein the indirect connection includes "connection via a wireless communication network".

The terms first, second, etc. are used to distinguish one component from another component, and the component is not limited by the terms described above.

An expression used in the singular encompasses the expression of the plural, unless it has a clearly different meaning in the context.

The reference numerals used in operations are used for descriptive convenience and are not intended to describe the order of operations and the operations may be performed in a different order unless otherwise stated.

Hereinafter, embodiments of the present disclosure will be described with reference to the accompanying drawings.

FIG. 1 is a control block diagram of an emotion adjustment system according to an embodiment.

An emotion adjustment system 1 according to an embodiment may refer to an artificial intelligence speaker, a home appliance equipped with a microphone, a vehicle, or the like.

Hereinafter, a case in which the emotion adjustment system 1 according to an embodiment is provided as part of a vehicle will be described as an example, but the emotion adjustment system 1 is not limited to implementation in a vehicle.

The emotion adjustment system 1 may include a microphone 10 to receive a user's voice, a controller 20 that identifies a user's emotions in response to processing the user's voice and controls a feedback device 30 by transmitting a control command corresponding to the user's emotional state, and the feedback device 30 that performs an operation corresponding to the control command transmitted from the controller 20.

The microphone 10 may receive the user's voice, perform processing such as amplification and noise reduction, and transmit the processed voice signal of the passenger to the controller 20.

When the emotion adjustment system 1 is a vehicle, the microphone 10 may be provided without limitation at a location capable of acquiring a user's voice signal located inside the vehicle, and a number of microphone(s) 10 is also not limited.

The controller 20 may include at least one memory 22 for storing various instructions and/or algorithms and/or programs and/or data for performing the above-described and below-described operations, and at least one processor 21 that performs an operation for controlling the operation of various components of the emotion adjustment system 1 based on various instructions and/or algorithms and/or programs and/or data stored in the memory 22.

The memory 22 may be implemented as at least one of a non-volatile memory devices such as a cache, read only memory (ROM), programmable ROM (PROM), erasable programmable ROM (EPROM), electrically erasable programmable ROM (EEPROM), and flash memory or a volatile memory device such as random access memory (RAM), or a storage medium such as a hard disk drive (HDD) or a CD-ROM in order to store various types of information. However, the present disclosure is not limited thereto.

The memory 22 may be implemented as a separate chip, or may be implemented as a single chip with a processor 21.

The feedback device 30 may include any device capable of providing feedback that may cause a user's emotional change. For this, the feedback device 30 may provide various types of feedback such as visual feedback, auditory feedback, tactile feedback, and olfactory feedback.

For example, the feedback device 30 may include a vibrating element 31 capable of providing tactile feedback to the user and a speaker 32 capable of providing auditory feedback, but is not limited thereto.

In particular, although not shown in the drawings, the feedback device 30 may include various components such as an air conditioner, a lighting device, or a display.

When the emotion adjustment system 1 is implemented in a vehicle, the vibrating element 31 may be provided on a steering wheel and/or a seat to provide tactile feedback to the user, and the speaker 32 may be provided inside the vehicle to provide auditory feedback to the user.

The vibrating element 31 may be provided without limitation as long as the vibrating element 31 is provided at one or more positions allowing the user to feel the vibration, and the speaker 32 may be provided without limitation as long as position(s) of the speaker 32 permit the user to hear sound emitted by the speaker 32. In particular, the vibrating element 31 refers to one or more vibrating elements, and the speaker 32 refers to one or more speakers.

The feedback device 30 may perform an operation corresponding to the control command transmitted from the controller 20.

In one embodiment, the microphone 10, the controller 20, and the feedback device 30 may communicate with each other by performing Controller Area Network (CAN) communication to transmit respective information, and may perform wired communication to transmit respective information. For example, when the emotion adjustment system 1 means a vehicle, for control of various electric loads mounted on a vehicle and communication between various electric loads, in the vehicle, a communication network including a body network, a multimedia network, and a chassis network is configured, and each of the networks separated from each other may be connected by the controller 20 in order to exchange CAN communication messages with each other.

As described above, the configuration of the emotion adjustment system 1 according to an embodiment and the operation and structure of each configuration have been described. Hereinafter, an emotion adjustment method using various configurations of the emotion adjustment system 1 will be described in detail.

Figure 2:
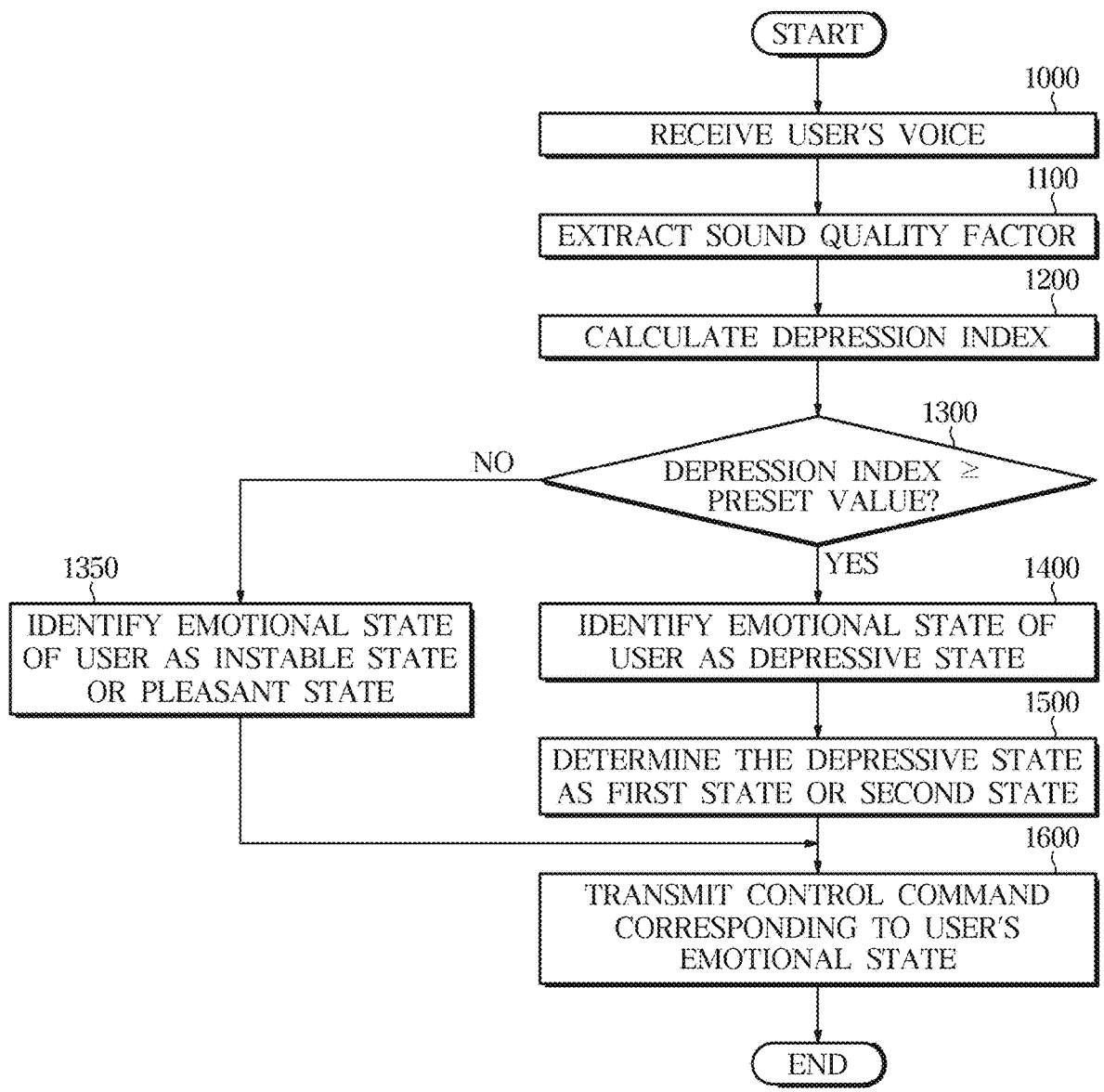
FIG. 2 is a flowchart of an emotion adjustment method according to an embodiment.
Figure 3:
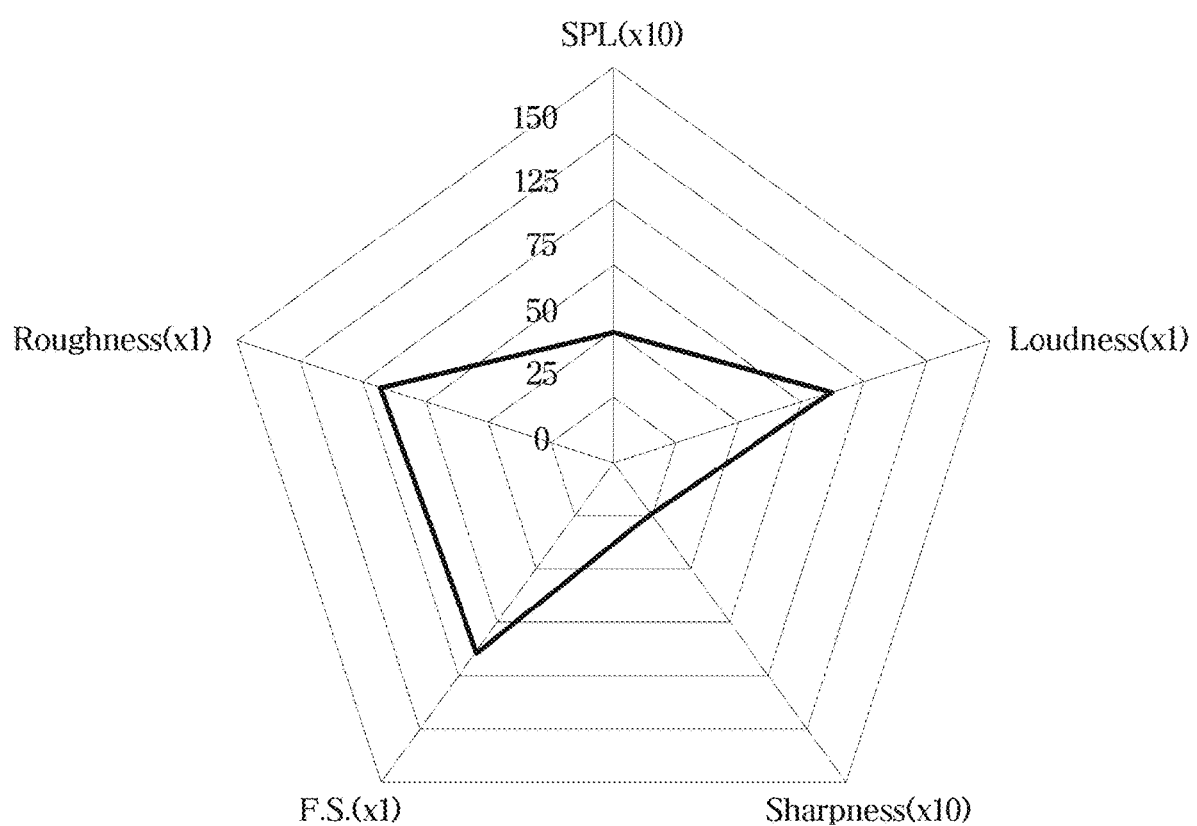
FIG. 3 is a diagram illustrating a correlation between a plurality of sound quality factors included in a user's voice.
Figure 4:
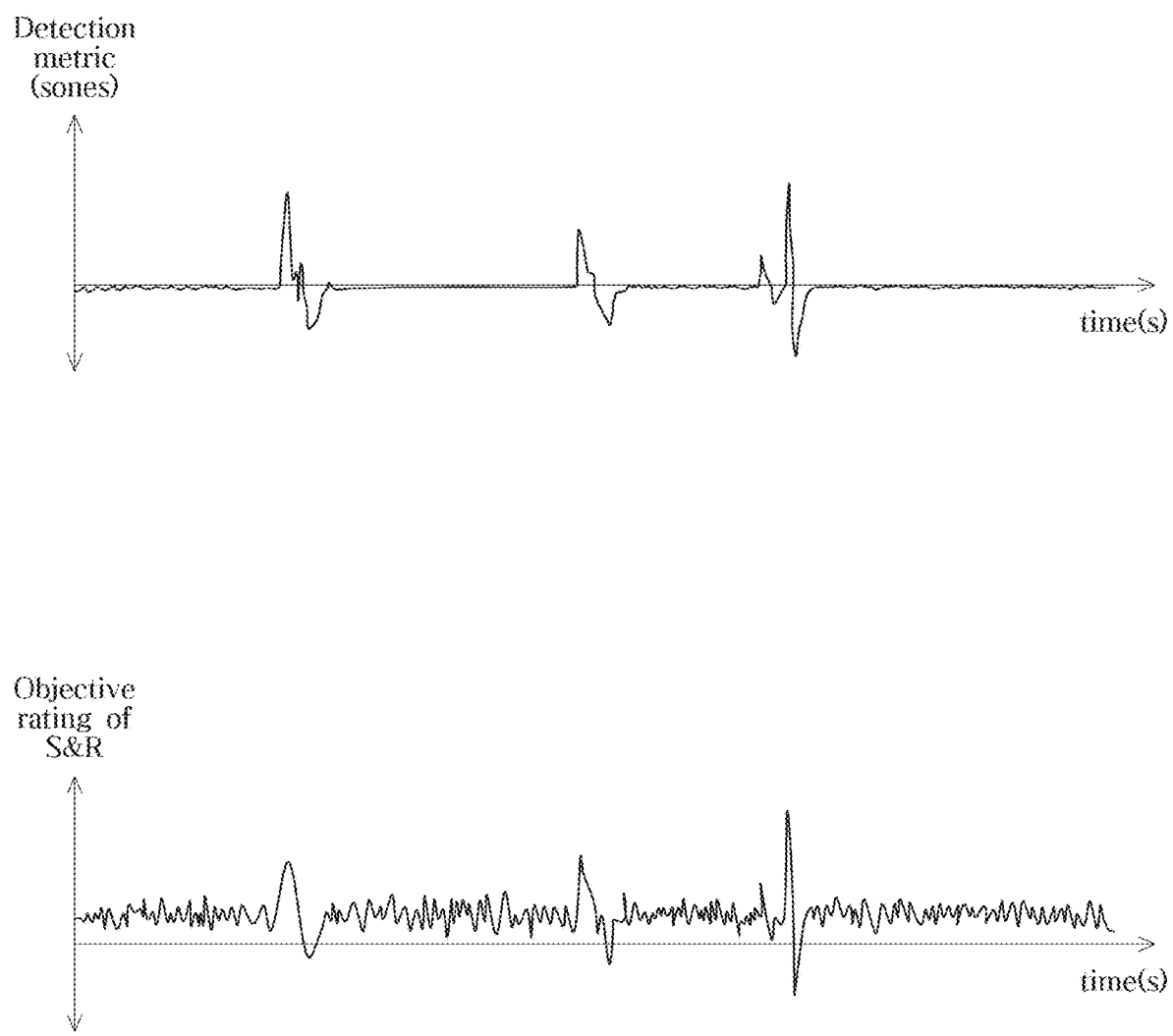
FIG. 4 is a diagram illustrating the result of calculating a depression index based on the user's voice.
Figure 5:
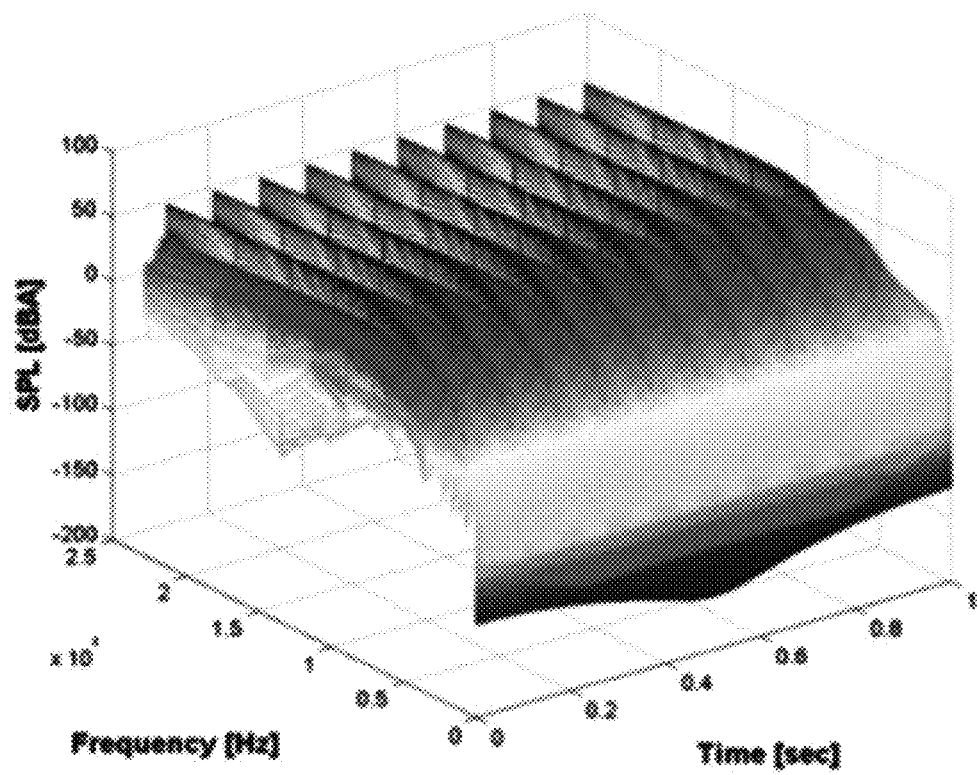
FIG. 5 is a diagram illustrating two examples of voices divided into depressive emotions.
Figure 5:
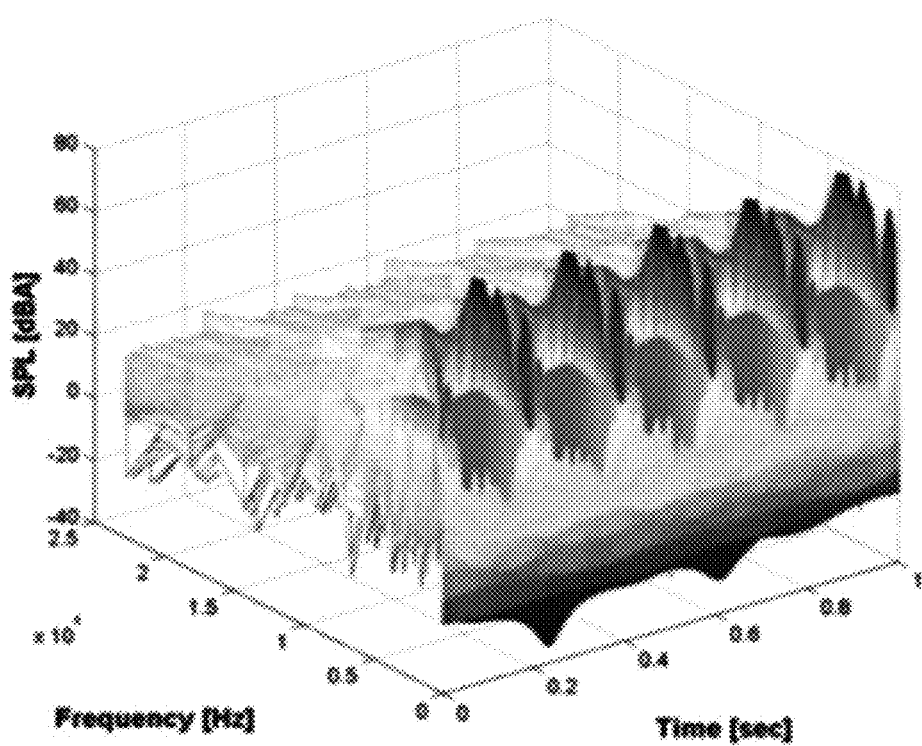
Figure 6:
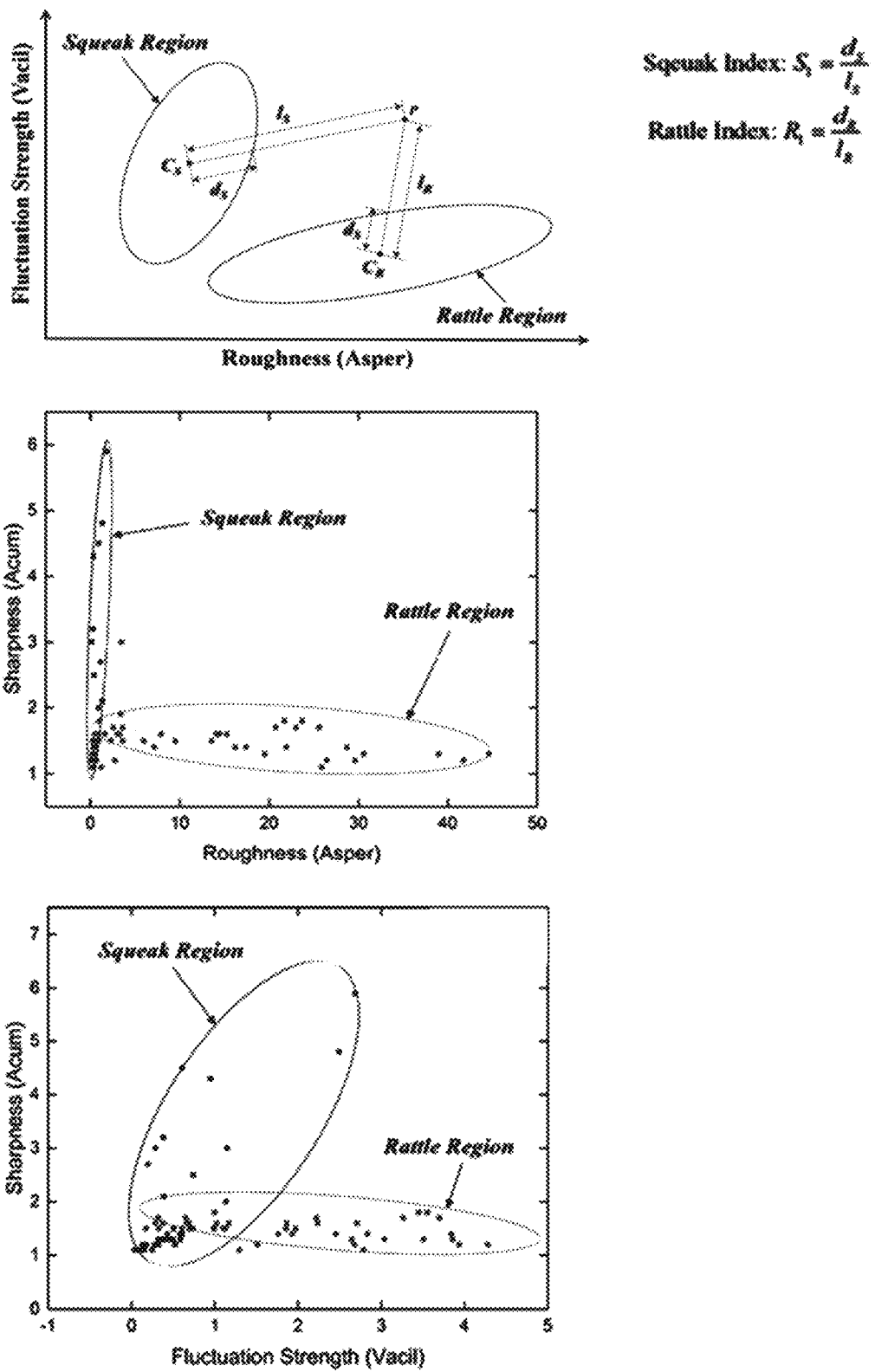
FIG. 6 is a diagram illustrating a method for calculating a noise index based on correlation between sound quality factors.

FIG. 2 is a flowchart of an emotion adjustment method according to an embodiment. FIG. 3 is a diagram illustrating a correlation between a plurality of sound quality factors included in a user's voice. FIG. 4 is a diagram illustrating the result of calculating a depression index based on the user's voice. FIG. 5 is a diagram illustrating two examples of voices divided into depressive emotions. FIG. 6 is a diagram illustrating a method for calculating a noise index based on correlation between sound quality factors.

Referring to FIG. 2, the microphone 10 may receive the user's voice and output it as an electrical signal, and the controller 20 may receive the user's voice signal output as an electrical signal from the microphone 10 (1000).

The controller 20 may process the user's voice and extract a plurality of sound quality factors in response to processing the user's voice (1100).

In particular, the processor 21 may extract sound quality factors of the user's voice received from the microphone 10 using a sound quality factor analysis program stored in the memory 22.

Referring to FIG. 3, the plurality of sound quality factors may include at least one of a sound pressure level, loudness, sharpness, roughness, or fluctuation strength.

Each of the plurality of sound quality factors may be quantified and extracted, and different weights may be given to each of the sound quality factors for correlation analysis between the sound quality factors.

Thereafter, the controller 20 may calculate a user's depression index based on at least one sound quality factor among a plurality of sound quality factors (1200). In particular, as provided herein, a "depression index" refers to a measurement based on emotional factors received from a user providing an indication of an emotional state of the user, such as whether the user exhibits symptoms of depression, i.e., a persistent feeling of sadness and loss of interest in the user.

For example, the controller 20 may calculate the user's depression index based on at least one of a sound pressure level or loudness, i.e., the controller 20 may calculate the user's depression index based on a change pattern of sound pressure level or loudness.

The memory 22 may store an algorithm including an equation for sound pressure level or loudness, and the processor 21 may calculate a depression index based on an algorithm stored in the memory 22.

As an example, the memory 22 may store the following [Equation 1] to [Equation 3].

[Equation 1]

$$N_{det} = N_{PTL} - N_t \quad (1)$$

[Equation 2]

$$N_{obj} = 2.9 * N'_{PTL} + 1.33 \quad (2)$$

[Equation 3]

$$N_t = 1.77 * n_{75} * (N_{PTL}) + 0.0022 \quad (3)$$

At this time, $N_{det}$ means a detection metric that is a quantitative depression index, $N_{PTL}$ means a Perceived Transient Loudness (the loudness of a perceived instantaneous sound) value with loudness corrected, $N_t$ means a detection threshold, which is a detection threshold, and $N_{obj}$ means objective rating, which is a qualitative depression index, $N'_{PTL}$ means the time history of Perceived Transient Loudness (the loudness of a perceived instantaneous sound), and $n_{75}$ is a percentile value and may mean a value used to analyze a sound property. Correlation of $n_{75}$ with $N_t$ and $N_{PTL}$ was confirmed through Jury test.

Also, the memory 22 may store [Algorithm 1] for determining the $N_{PTL}$ value.

[Algorithm 1]

if $N_{inst}(i) \geq N_{inst}(i-1)$ then $N_{PTL}(i) = (1-\alpha_a) * N_{PTL}(i-1) + \alpha_a * N_{inst}(i)$ else $N_{PTL}(i) = (1-\alpha_r) * N_{PTL}(i-1) + \alpha_r * N_{inst}(i) \quad (4)$ In this case, $\alpha_a$ may mean an attack time constant (forward masking), and $\alpha_r$ may mean a release time constant (backward masking). $\alpha_a$ and $\alpha_r$ are values to reflect the masking effect of ambient noise in order to recognize the user's voice.

The processor 21 may calculate the detection metric value, which is a quantitative depression index, identify the emotional state of the user as a pleasant state when the detection metric value is 0 or less, identify the emotional state of the user as an instable state when the detection metric value is greater than 0 and less than or equal to 0.2, and identify the emotional state of the user as a depressive state when the detection metric value is greater than 0.2.

In addition, the processor 21 may calculate the objective rating value, which is a qualitative depression index, and identifies that the emotional state of the user is closer to the depressive state as the objective rating value is higher, and identify that the emotional state of the user is closer to the pleasant state as the objective rating value is lower.

That is, the depression index may include both a quantitative depression index and a qualitative depression index, and the processor 21 may identify the emotional state of the user as a depressive state when the depression index is greater than or equal to a preset value.

In particular, the processor 21 may identify the emotional state of the user as a depressive state when the quantitative depression index is greater than or equal to the first preset value or the qualitative depression index is greater than or equal to the second preset value (YES in 1300) (1400).

On the contrary, the processor 21 may identify the emotional state of the user as an instable state or a pleasant state when the quantitative depression index is less than the first preset value or the qualitative depression index is less than the second preset value (NO in 1300). There is (1350). For example, the processor 21 may identify the emotional state of the user as a pleasant state when the quantitative depression index is less than 0, and may identify the emotional state of the user as an instable state when the quantitative depression index is greater than 0 and less than 0.2.

Referring to FIG. 4, the processor 21 may check the result of calculating the detection metric value and the objective rating value over time. As described above, the processor 21 may identify the emotional state of the user by calculating the detection metric value and the objective rating value of the user's voice in real time.

Although not shown in FIG. 2, the memory 22 may store an algorithm related to a neural network learned by using a plurality of sound quality factors and a Frontal Alpha Asymmetry (FAA) value, which is an index indicating the user's emotion, as training data, and the processor 21 may identify the emotional state of the user from a plurality of sound quality factors using a pre-trained neural network stored in the memory 22.

Since the neural network refers to machine learning in the shape of a neural structure capable of performing deep learning, the weight and bias corresponding to the configuration of the neural network are continuously changed to improve the reliability of learning.

As described above, the controller 20 may identify whether the emotional state of the user is a depressive state using a pre-trained neural network.

In this case, the emotional state of the user may be expressed using Russell's emotional model. Russell's emotional model is represented as a two-dimensional graph based on the x-axis (positivity) and y-axis (excitability), and divides emotions into 8 areas: joy (0 degree), excitement (45 degree), arousal (90 degree), pain (135 degree), discomfort (180 degree), depression (225 degree), drowsiness (270 degree), and relaxation (315 degree). In addition, the 8 areas are divided into a total of 28 emotions and are classified into similar emotions belonging to the 8 areas.

At this time, when the emotional state of the user is identified using the emotional model, when the user's positivity and excitability at the first time point are the same as the user's positivity and excitability at the second time point, respectively, the emotional state of the user at the first time point and the second time point may be identified as the same emotional state.

Referring again to FIG. 2, the controller 20 may determine the depressive state as a first state or a second state based on the correlation between at least two sound quality factors among a plurality of sound quality factors (1500).

That is, even if the user's emotional state is identified as a "depressive state", the controller 20 further subdivides this "depressive state", and distinguish whether the user's depressive state is a state in which the user may feel "under the weather" (hereinafter referred to as a first state), or a state in which the user may feel annoyed (hereinafter referred to as a second state).

Referring to FIG. 5, when the user's voice is analyzed as shown in the pattern below, the user's emotional state can be determined as the first state, and when the user's voice is analyzed as in the pattern above, the user's emotional state can be determined as the second state.

That is, when a single peak occurs in the frequency domain and/or time band as a result of analyzing the user's voice, the user's emotional state can be determined as the first state, and as a result of analyzing the user's voice, if there is a broadband characteristic in the frequency domain, the emotional state of the user can be determined as the second state. According to the emotion adjustment system 1 according to an embodiment, correlation between a plurality of sound quality factors is used to determine the depressive state as the first state and the second state.

In particular, the controller 20 may calculate the noise index of the user's voice based on the correlation between sharpness, roughness, and fluctuation strength among a plurality of sound quality factors, and determine the depressive state as the first state or the second state based on the noise index.

In this case, the noise index may include a rattle index that quantifies the degree of inclusion of a rattle sound and a squeak index that quantifies the degree of inclusion of a squeak sound.

To this end, the memory 22 may store a lookup table and/or algorithm capable of calculating a noise index based on a correlation between a plurality of sound quality factors.

Referring to FIG. 6, According to the correlation between sharpness and roughness, the correlation between roughness and fluctuation strength, and the correlation between sharpness and fluctuation strength, the graphs that can derive whether the user's voice is included in the rattle region or the squeak region, and equation that can calculate the rattle index and the squeak index can be checked.

The controller 20 can determine whether the user's voice is included in the rattle region or the squeak region based on the correlation between sharpness, roughness and fluctuation strength, determine the emotional state of the user identified as a depressive state as a first state when the user's voice belongs to the rattle region, and determine the emotional state of the user identified as the depressive state as the second state when the user's voice belongs to the squeak region.

In addition, the controller 20 may calculate the rattle index and the squeak index of the user's voice based on the equation shown in FIG. 6, and determine the depressive state as the first state or the second state based on the ratio between the rattle index and the squeak index.

At this time, the controller 20 may determine the depressive state as the first state when the rattle index is greater than the squeak index, and the depressive state into the second state when the squeak index is greater than the rattle index.

For example, when the roughness value is 0.269 (Asper), the fluctuation strength value is 0.396 (Vacil), and the sharpness value is 1.3 (Acum), the controller 20 may calculate the squeak index as 1.741 and the rattle index as 0.510 using an algorithm including a lookup-table and/or equation stored in the memory 22.

As above, when the squeak index is calculated as 1.741 and the rattle index is calculated as 0.510, the controller 20 can determine the emotional state of the user identified as the depressive state as the second state.

That is, the controller 20 may finally identify the emotional state of the user identified as the depressive state as the first state or the second state.

The controller 20 may transmit a control command corresponding to the user's emotional state in response to finally identifying the user's emotional state (1600).

To this end, the memory 22 may store operation information of the feedback device 30 corresponding to the emotional state of the user.

For example, the memory 22 may store a first control command for controlling the vibrating element 31 to vibrate at a first frequency and first intensity as a control command corresponding to the first state, and store a second control command for controlling the vibrating element 31 to vibrate at a second frequency and second intensity as a control command corresponding to the second state. In this case, the first frequency may be smaller than the second frequency, and the first intensity may be smaller than the second intensity.

Accordingly, when the user's emotional state is identified as the first state, the controller 20 transmits a first control command to cause the vibrating element 31 to vibrate at a first frequency and first intensity. When the emotional state of the user is identified as the second state, the controller 20 may transmit a second control command to cause the vibrating element 31 to vibrate at a second frequency and second intensity.

The feedback device 30 may perform an operation corresponding to the control command transmitted from the controller 20. For example, the vibrating element 31 may vibrate at a first frequency and first intensity in response to receiving a first control command transmitted from the controller 20, and the vibrating element 31 may vibrate at a second frequency and second intensity in response to receiving the second control command transmitted from the controller 20.

According to the emotion adjustment system 1 according to an embodiment, when the emotional state of the user is identified as the first state, the user can be stabilized by providing the user with a vibration with a relatively low frequency and weak intensity, and when the emotional state of the user is identified as the second state, the user's positivity and/or excitability may be improved by providing the user with a vibration having a relatively high frequency and high intensity.

In addition, the memory 22 may store a first control command for controlling the speaker 32 to play the first sound source as a control command corresponding to the first state, and may store a second control command for controlling the speaker 32 to play the second sound source as a control command corresponding to the second state. In this case, the frequency band of the first sound source may be narrower than the frequency band of the second sound source.

Accordingly, when the emotional state of the user is identified as the first state, the controller 20 may transmit a first control command to cause the speaker 32 to play the first sound source. When the emotional state of the user is identified as the second state, the controller 20 may transmit a second control command to cause the speaker 32 to play the second sound source.

The feedback device 30 may perform an operation corresponding to the control command transmitted from the controller 20. For example, the speaker 32 may output a first sound source in response to receiving the first control command transmitted from the controller 20, and may output a second sound source in response to receiving the second control command transmitted from the controller 20.

According to the emotion adjustment system 1 according to an embodiment, when the user's emotional state is identified as the first state, it is possible to promote the user's stability by providing a quiet and emotional healing sound to the user, and when the user's emotional state is identified as the second state, the user's positivity and/or excitability level may be improved by providing the user with a light and moving healing sound.

According to the present disclosure, even if the emotional state of the user at the first time point and the emotional state of the user at the second time point are classified into the same emotional state (eg, depressive state), by dividing the same emotional state into a first state and a second state through correlation between a plurality of sound quality factors, the user's emotions can be more closely identified. Accordingly, it is possible to provide a more satisfactory feedback to the user.

According to the present disclosure, by identifying an emotion using only the user's voice, it is possible to prevent an increase in cost due to an increase in components for emotion determination.

In addition, it is possible to provide more suitable feedback to the user by subdividing and classifying the user's negative emotions.

Meanwhile, the disclosed embodiments may be implemented in the form of a recording medium storing instructions that are executable by a computer. The instructions may be stored in the form of a program code, and when executed by a processor, the instructions may generate a program module to perform operations of the disclosed embodiments. The recording medium may be implemented as a computer-readable recording medium.

The computer-readable recording medium may include all kinds of recording media storing commands that can be interpreted by a computer. For example, the computer-readable recording medium may be ROM, RAM, a magnetic tape, a magnetic disc, flash memory, an optical data storage device, etc.

The embodiments of the disclosure have thus far been described with reference to the accompanying drawings. It will be obvious to those of ordinary skill in the art that the disclosure may be practiced in other forms than the exemplary embodiments as described above without changing the technical idea or essential features of the disclosure. The disclosed embodiments are illustrative and should not be construed as limiting.

What is claimed is:

1. An emotion adjustment system, comprising:
   a microphone configured to receive a user's voice;
   a controller configured to extract a plurality of sound quality factors in response to processing the user's voice, calculate a depression index of the user based on at least one sound quality factor among the plurality of sound quality factors, identify an emotional state of the user as a depressive state when the depression index is a preset value or more, determine the depressive state as a first state or a second state based on a correlation between at least two sound quality factors among the plurality of sound quality factors, and transmit a control command corresponding to the emotional state of the user identified as the first state or the second state; and
   a feedback device configured to perform an operation corresponding to the control command,
   wherein the plurality of sound quality factors comprises a sharpness, a roughness, and a fluctuation strength,
   wherein the controller is configured to calculate a noise index of the user's voice based on a correlation between the sharpness, the roughness, and the fluctuation strength, and determine the depressive state as the first state or the second state based on the noise index,
   wherein the noise index comprises a rattle index and a squeak index, and
   wherein the controller is configured to determine the depressive state as the first state or the second state based on a ratio between the rattle index and the squeak index.

2. The emotion adjustment system of claim 1, wherein the plurality of sound quality factors further comprise at least one of a sound pressure level or a loudness.

3. The emotion adjustment system of claim 2, wherein the controller is configured to calculate the depression index of the user based on at least one of the sound pressure level or the loudness.

4. The emotion adjustment system of claim 3, wherein the controller is configured to calculate the depression index of the user based on a change pattern of the sound pressure level or the loudness.

5. The emotion adjustment system of claim 1, wherein the controller is configured to determine the depressive state as the first state when the rattle index is greater than the squeak index, and determine the depressive state as the second state when the squeak index is greater than the rattle index.

6. The emotion adjustment system of claim 5, wherein the feedback device comprises a vibrating element, and
   the controller is configured to transmit a first control command to cause the vibrating element to vibrate at a first frequency and a first intensity when the emotional state of the user is identified as the first state and transmit a second control command to cause the vibrating element to vibrate at a second frequency and a second intensity when the emotional state of the user is identified as the second state, and
   the first frequency is less than the second frequency and the first intensity is less than the second intensity.

7. The emotion adjustment system of claim 5, wherein the feedback device comprises a speaker, and
   the controller is configured to transmit a first control command to cause the speaker to play a first sound source when the emotional state of the user is identified as the first state and transmit a second control command to cause the speaker to play a second sound source when the emotional state of the user is identified as the second state, and
   a frequency band of the first sound source is narrower than a frequency band of the second sound source.

8. The emotion adjustment system of claim 1, wherein the controller is configured to identify the emotional state of the user as an instable state or a pleasant state when the depression index is less than the preset value, and transmit a control command corresponding to the emotional state of the user identified as the instable state or the pleasant state.

9. An emotion adjustment method, comprising:
   receiving, by a microphone, a user's voice;

extracting, by a controller, a plurality of sound quality factors in response to processing the user's voice;

calculating, by the controller, a depression index of the user based on at least one sound quality factor among the plurality of sound quality factors;

identifying, by the controller, an emotional state of the user as a depressive state when the depression index is a preset value or more;

determining, by the controller, the depressive state as a first state or a second state based on a correlation between at least two sound quality factors among the plurality of sound quality factors;

transmitting, by the controller, a control command corresponding to the emotional state of the user identified as the first state or the second state; and performing, by a feedback device, an operation corresponding to the control command, wherein the plurality of sound quality factors comprises a sharpness, a roughness, and a fluctuation strength, wherein determining the depressive state as the first state or the second state comprises:
calculating a noise index of the user's voice based on a correlation between the sharpness, the roughness, and the fluctuation strength; and
determining the depressive state as the first state or the second state based on the noise index, wherein the noise index comprises a rattle index and a squeak index, and wherein determining the depressive state as the first state or the second state based on the noise index comprises:
determining the depressive state as the first state or the second state based on a ratio between the rattle index and the squeak index.

10. The emotion adjustment method of claim 9, wherein the plurality of sound quality factors comprise at least one of a sound pressure level or a loudness.

11. The emotion adjustment method of claim 10, wherein calculating the depression index of the user comprises:
calculating the depression index of the user based on at least one of the sound pressure level or the loudness.

12. The emotion adjustment method of claim 11, wherein calculating the depression index of the user comprises:
calculating the depression index of the user based on a change pattern of the sound pressure level or the loudness.

13. The emotion adjustment method of claim 9, wherein determining the depressive state as the first state or the second state based on the ratio between the rattle index and the squeak index comprises:
determining the depressive state as the first state when the rattle index is greater than the squeak index, and determining the depressive state as the second state when the squeak index is greater than the rattle index.

14. The emotion adjustment method of claim 13, wherein the feedback device comprises a vibrating element, and
wherein the transmitting the control command corresponding to the emotional state of the user identified as the first state or the second state comprises:
transmitting a first control command to cause the vibrating element to vibrate at a first frequency and a first intensity when the emotional state of the user is identified as the first state; and
transmitting a second control command to cause the vibrating element to vibrate at a second frequency and a second intensity when the emotional state of the user is identified as the second state, and
the first frequency is less than the second frequency and the first intensity is less than the second intensity.

15. The emotion adjustment method of claim 13, wherein the feedback device comprises a speaker, and wherein transmitting the control command corresponding to the emotional state of the user identified as the first state or the second state comprises:
transmitting a first control command to cause the speaker to play a first sound source when the emotional state of the user is identified as the first state; and
transmitting a second control command to cause the speaker to play a second sound source when the emotional state of the user is identified as the second state, and
a frequency band of the first sound source is narrower than a frequency band of the second sound source.

16. The emotion adjustment method of claim 9, further comprising:
identifying the emotional state of the user as an instable state or a pleasant state when the depression index is less than the preset value; and
transmitting a control command corresponding to the emotional state of the user identified as the instable state or the pleasant state.

* * * * *